United States Patent [19]

Nedelec et al.

[11] Patent Number: 4,493,836
[45] Date of Patent: Jan. 15, 1985

[54] 9-OXALYSERGIC ACID DERIVATIVES AND USES THEREOF

[75] Inventors: Lucien Nedelec, Le Raincy; André Pierdet, Villemomble; Patrick Fauveau, Livry-Gargan, all of France

[73] Assignee: Roussel Uclaf, Paris, France

[21] Appl. No.: 493,355

[22] Filed: May 10, 1983

[30] Foreign Application Priority Data

May 12, 1982 [FR] France .................. 82 08249

[51] Int. Cl.³ .................. A61K 31/535; C07D 498/04
[52] U.S. Cl. .................. 424/248.4; 424/248.52; 424/248.53; 424/248.54; 424/248.55; 424/248.56; 424/248.57; 424/248.58; 544/73; 544/99
[58] Field of Search .................. 544/73, 99; 424/248.4, 424/248.52, 248.53, 248.54, 248.55, 248.56, 248.57, 248.58

[56] References Cited

U.S. PATENT DOCUMENTS 4,238,486 12/1980 Jones .................. 544/99 X
4,318,910 3/1982 Nedelec et al. .................. 544/99 X Primary Examiner—Richard L. Raymond
Attorney, Agent, or Firm—Charles A. Muserlian

[57] ABSTRACT

Novel derivatives of 9-oxalysergic acid of the formula

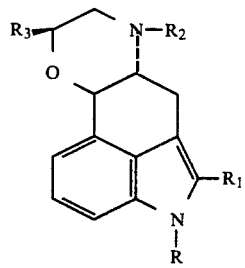

wherein R is selected from the group consisting of hydrogen and alkyl of 1 to 4 carbon atoms, $R_1$ is selected from the group consisting of hydrogen, chlorine and bromine, $R_2$ is selected from the group consisting of hydrogen, alkyl of 1 to 4 carbon atoms, aralkyl of 7 to 12 carbon atoms and cycloalkylalkyl of 4 to 7 carbon atoms, $R_3$ is selected from the group consisting of —CH$_2$OH, alkylthiomethyl with 1 to 4 alkyl carbon atoms, —CH$_2$CN, —COOH, —COOAlk and

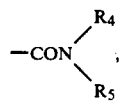

Alk is alkyl of 1 to 5 carbon atoms, $R_4$ is selected from the group consisting of hydrogen and alkyl of 1 to 5 carbon atoms, $R_5$ is alkyl of 1 to 5 carbon atoms or $R_4$ and $R_5$ together with the nitrogen form a saturated heterocycle optionally containing another heteroatom and their non-toxic, pharmaceutically acceptable acid addition salts having essentially dopaminergic agonist activity, inhibiting activity of prolactin secretion, serotoninergic activity and antihypertensive activity and their preparation.

17 Claims, No Drawings

9-OXALYSERGIC ACID DERIVATIVES AND USES THEREOF

STATE OF THE ART

The 9th Edition of Merck Index describes lysergic acid and U.S. Pat. No. 4,318,910 and published European patent application Ser. No. 0033,767 describe indolobenzoxazines.

OBJECTS OF THE INVENTION

It is an object of the invention to provide the novel compounds of formula I and their non-toxic, pharmaceutically acceptable acid addition salts and their preparation.

It is another object of the invention to provide novel antihypertensive and dopaminergic agonist compositions and a method of treating hypertension and of inducing dopaminergic agonist activity in warm-blooded animals.

It is a further object of the invention to provide novel compositions for treating hypersecretion of prolactin and a method of treating hypersecretion of prolactin in warm-blooded animals.

It is an additional object of the invention to provide compositions for treating cerebral hypoxia and a method of increasing cerebral blood flow in warm-blooded animals.

These and other objects and advantages of the invention will become obvious from the following description.

THE INVENTION

The novel compounds of the invention are selected from the group consisting of derivatives of 9-oxalysergic acid of the formula.

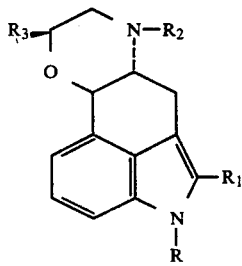

I wherein R is selected from the group consisting of hydrogen and alkyl of 1 to 4 carbon atoms, $R_1$ is selected from the group consisting of hydrogen, chlorine and bromine, $R_2$ is selected from the group consisting of hydrogen, alkyl of 1 to 4 carbon atoms, aralkyl of 7 to 12 carbon atoms and cycloalkylalkyl of 4 to 7 carbon atoms, $R_3$ is selected from the group consisting of —CH$_2$OH, alkylthiomethyl with 1 to 4 alkyl carbon atoms —CH$_2$CN, —COOH, —COOAlk and

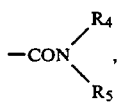

Alk is alkyl of 1 to 5 carbon atoms, $R_4$ is selected from the group consisting of hydrogen and alkyl of 1 to 4 carbon atoms, $R_5$ is alkyl of 1 to 4 carbon atoms or $R_4$ and $R_5$ together with the nitrogen form a saturated heterocycle optionally containing another heteroatom and their non-toxic, pharmaceutically acceptable acid addition salts.

Examples of alkyl of 1 to 4 carbon atoms are preferable methyl, ethyl, propyl and isopropyl and examples of Alk is methyl, ethyl, propyl and isopropyl. Examples of aralkyl of 7 to 12 carbon atoms are benzyl and phenethyl optionally substituted with at least one member of the group consisting of halogens, methyl, ethyl, methoxy, —OH and —CF$_3$ and cycloalkylalkyl is preferably cyclopropylmethyl. Examples of alkylthiomethyl are n-propylthiomethyl, ethylthiomethyl and especially methylthiomethyl. Examples of heterocycles formed by

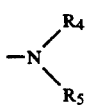

are pyrrolidino, piperidino, morpholino or piperazino and the second ring nitrogen atom if present, may be optionally substituted with alkyl of 1 to 4 carbon atoms.

Examples of suitable acids for the non-toxic, pharmaceutically acceptable acid addition salts are inorganic acids such as hydrochloric acid, hydrobromic acid, nitric acid, sulfuric acid and phosphoric acid and organic acids such as formic acid, acetic acid, propionic acid, benzoic acid, maleic acid, fumaric acid, succinic acid, tartaric acid, citric acid, oxalic acid, glyoxylic acid, aspartic acid, alkane sulfonic acids such as methane sulfonic acid and ethane sulfonic acid, aryl sulfonic acids such as benzene sulfonic acid and p-toluene sulfonic acid and aryl carboxylic acids.

Among the preferred compounds of formula I are those wherein R is hydrogen, those wherein $R_1$ is hydrogen, chlorine or bromine, those wherein $R_2$ is alkyl of 1 to 4 carbon atoms and those wherein $R_3$ is —CH$_2$OH, —CH$_2$S—CH$_3$, —CH$_2$CN, —COOH, —COOAlk or

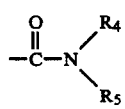

wherein Alk, $R_4$ and $R_5$ are alkyl of 1 to 4 carbon atoms and their nontoxic, pharmaceutically acceptable acid addition salts.

Preferred compounds of formula I are [6a RS (6aα, 9β, 10aβ)] 4,6,6a,8,9,10a-hexahydro-7-methyl-7H-indolo(3,4-g,h) 1,4-benzoxazine-9-methanol, [6a RS (6aα,9β,10aβ)] N,N-diethyl-4,6,6a,8,9,10a-hexahydro-7-methyl-7H-indolo-(3,4-g,h)1,4-benzoxazine-9-carboxamide and [6a RS (6aα,9β,10aβ)] 4,6,6a,8,9,10a-hexahydro-7-methyl-9-methylthiomethyl-7H-indolo (3,4-g,h) 1,4-benzoxazine and their non-toxic, pharmaceutically acceptable acid addition salts.

The novel process of the invention for the preparation of compounds of formula I comprises debenzylating a compound of the formula

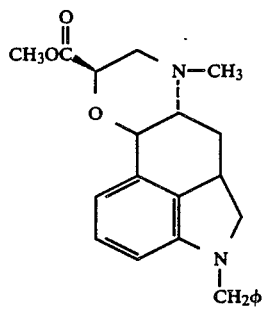                                II to obtain a compound of the formula

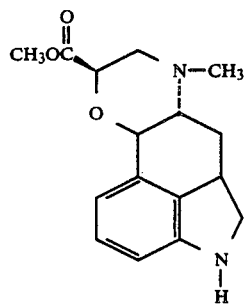                                III subjecting the latter to deshydrogenation to obtain a compound of the formula

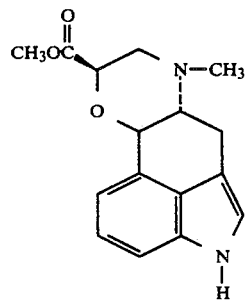                                $I_A$ which may be isolated and, if desired, salified or subjecting the said compound to desmethylation to obtain compound of the formula

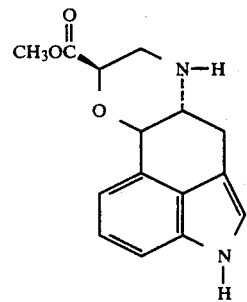                                $I_B$ which may be isolated and, if desired, salified or reacting a compound of formula $I_B$ with an alkylation agent to obtain a compound of the formula

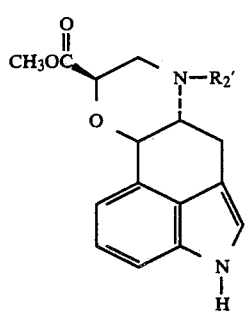                                $I_C$ wherein $R_2'$ is $R_2$ other than hydrogen which may be isolated and, if desired, salified or reacting the compound of formula $I_C$ with an alkali metal amide and then with an alkyl halide of the formula Hal—R'                                IV wherein R' is R other than hydrogen and Hal is chlorine, bromine or iodine to obtain a compound of the formula

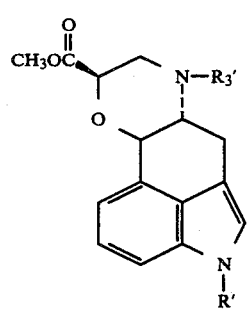                                $I_D$ which may be isolated and, if desired, salified or reacted with a halogenation agent to obtain a compound of the formula

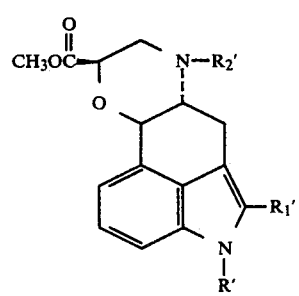                                $I_E$ wherein $R_1'$ is chlorine or bromine and $R_2'$ and R' have the above definitions which may be isolated and, if desired, salified or reacting the compound of formula $I_C$ with a halogenating agent to form a compound of the formula

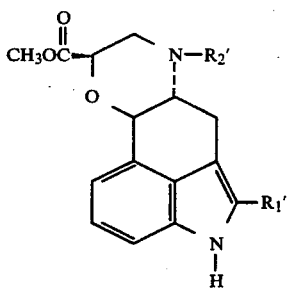

wherein R₂' and R₁' have the above definition which may be isolated and, if desired, salified or saponifying the compound of formula $I_A$ to obtain a compound of the formula

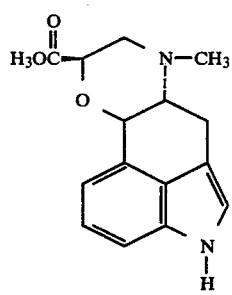

which may be isolated and, if desired, salified or reacting the latter with an amine of the formula

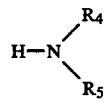

wherein R₄ and R₅ have the above definitions to obtain a compound of the formula

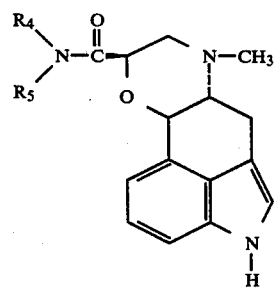

which may be isolated and, if desired, salified or subjecting the compound of formula $I_C$ to esterification to obtain a compound of the formula

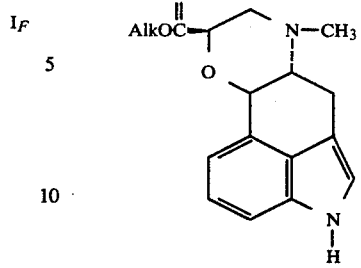

wherein Alk has the above definition or reducing the compound of formula $I_A$ to obtain a compound of the formula

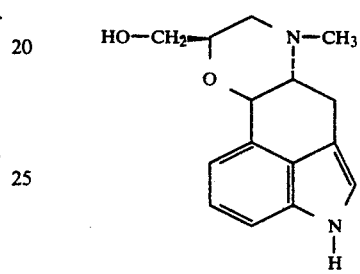

which may be isolated and, if desired, salified or reacting the latter with methane sulfonyl chloride or p-toluene sulfonyl chloride to obtain a compound of the formula

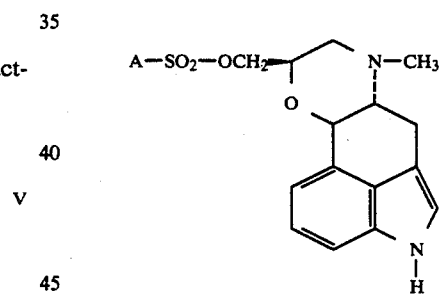

wherein A is methyl or p-tolyl which is reacted with an alkylmercaptan or an alkali metal cyanide to obtain a compound of the formula

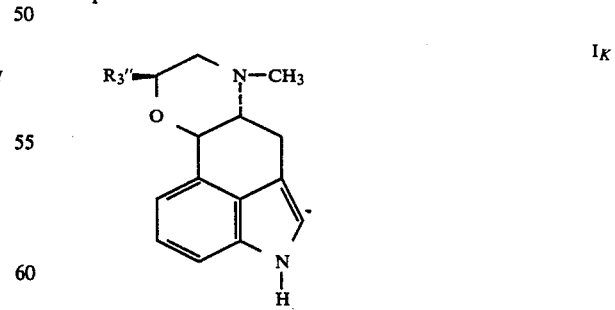

wherein R₃'' is alkylthiomethyl or CNCH₂— which may be isolated and, if desired, salified and if desired, the compounds of formulae $I_G$, $I_H$, $I_I$, $I_J$ and $I_K$ may be subjected to the same reactions as the compounds of formula $I_A$ to obtain the corresponding compounds of formula I which may be isolated and, if desired, salified.

The debenzylation of the compounds of formula II is preferably effected by catalytic hydrogenation such as with a catalyst like palladium in acetic acid. The dehydrogenation of the compounds of formula III is preferably effected with an oxidizing agent such as manganese dioxide but may also be effected with palladium in refluxing xylene. The demethylation of the compound of formula I$_A$ is preferably effected with cyanogen bromide followed by reduction such as with zinc in acetic acid.

The alkylation of the compounds of formula I$_B$ is preferably effected with an alkyl halide, especially alkyl iodide, in the presence of a condensation agent such as an alkali metal carbonate. For methylation, it is advantageous to use formal in a solvent such as acetonitrile in the presence of a reducing agent such as sodium cyanoborohydride and especially sodium borohydride.

The halide of formula IV is preferably chloride or bromide but especially iodide and is reacted after action especially in ammonium hydroxide with an alkali metal amide, especially sodium amide to form the compound of formula I$_C$.

The halogenation of the compounds of formulae I$_C$ and I$_D$ may be effected with N-chloro-succinimide for chlorination or with N-bromo-succinimide or preferably with a complex of pyrrolidone bromide of the formula

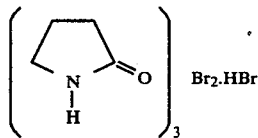

for bromination.

The saponification of the compound of formula I$_A$ is preferably effected with a strong base such as 2N sodium hydroxide but may equally be effected in an acid medium such as mineral acids like dilute hydrochloric acid in a solvent such as an alkanol of 1 to 5 carbon atoms, especially ethanol.

The reaction of the compound of formula I$_G$ with an amine of formula V to obtain the compound of formula I$_H$ is preferably effected after activation of the carboxylic acid function by the formation of a mixed anhydride, for example by the action of trifluoroacetic anhydride or of an alkyl halogenoformate such as isobutyl chloroformate.

The esterification of compound of formula I$_G$ is effected in usual condition such as by action of an aliphatic alcohol of 1 to 5 carbon atoms on the acid or on a functional derivative such as a halide or an anhydride.

The reduction of the compound of formula I$_A$ is preferably effected with sodium borohydride at reflux in a solvent such as dioxane and methanol. Equally useful are other reducing agents such as lithium aluminium hydride or sodium cyanoborohydride. The reaction of the compound of formula I$_J$ with methane sulfonyl chloride is preferably effected in pyridine at room temperature.

The reaction of the compound of formula VI with an alkylmercaptan is preferably effected at room temperature in a solvent such as dimethylacetamide in the presence of sodium hydride. The alkylmercaptan is preferably methylmercaptan. The alkali metal cyanide reacted with the compound of formula VI is preferably potassium cyanide and the reaction is preferably effected in a solvent such as dimethylformamide.

In a preferred mode of the invention, the compound of formula II is prepared by reacting a compound of the formula

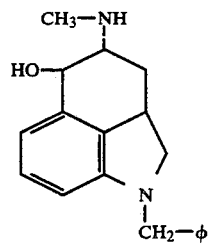

VII with an alkyl glycidate of the formula

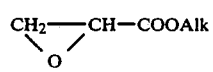

VIII wherein Alk is alkyl of 1 to 4 carbon atoms to obtain a compound of the compound

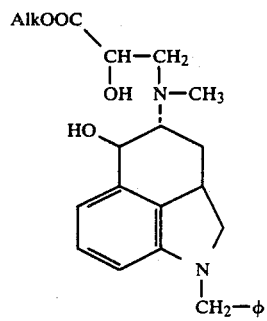

IX cyclizing the latter to obtain a compound of the formula

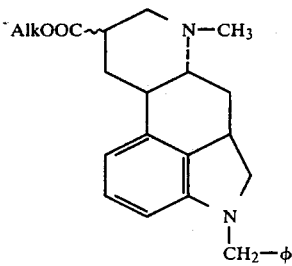

X wherein the wavy line indicates the group is in the 9α- or 9β-position, epimerizing the 9α-isomer and esterifying the acid obtained with the substituent in the 9β-position to obtain the compound of formula II.

The alkyl glycidate of formula VIII is preferably ethyl glycidate and the reaction is effected at reflux in an alkanol of 1 to 4 carbon atoms, preferably with an alkanol with the same number of carbon atoms as the alkyl portion of the compound of formula VIII. The cyclization of the compound of formula IX is effected with N-chloro-diisopropylamine in the presence of hexamethylphosphoramine. Especially useful is the action of carbon tetrachloride in the presence of triphenylphosphine or hexamethylphosphoramine followed by cyclization of the chlorinated derivative with sodium hydride in a solvent such as dimethoxyethane.

The epimenization of the compound of formula X with 9α and 9β-structures is effected by known methods, preferably in a basic medium by reaction with an alkali metal alcoholate, especially sodium ethylate at reflux for one to four hours. The esterification leading to the compound of formula II is preferably effected with diazomethane.

The compounds of formula I have a basic character except for those wherein $R_3$ is —COOH and the acid addition salts of the basic compounds are formed by reaction with approximately stoichiometric amounts of the desired acid and the compounds of formula I and the free base need not be isolated.

The novel antihypertensive and dopaminergic agonist compositions of the invention are comprised of an antihypertensively and dopaminergic agonistically effective amount of at least one compound of formula I and their non-toxic, pharmaceutically acceptable acid addition salts and an inert pharmaceutical carrier. The compositions may be in the form of tablets, dragees, gelules, granules, suppositories and injectable solutions or suspensions.

Examples of suitable pharmaceutical carriers are talc, arabic gum, lactose, starch, magnesium stearate, cacao butter, fatty bodies of animal or vegetable origin, aqueous and non-aqueous vehicles, paraffinic derivatives, glycols, diverse wetting agents, dispersants or emulsifiers and preservatives.

The compositions are useful for the treatment of neurological syndromes of extra-pyramidal origin such as for the treatment of Parkinson disease and the treatment of postencephalitic parkinson syndromes. They are also useful for the treatment of prolactin hypersecretion by antehypophysis such as for the treatment of hypogonadism in the male or female. They are also useful for the treatment of cerebral senescence or manifestation of a cerebral hypoxia.

Due to their hypotensive and antihypertensive activity, the compositions are useful for the treatment of essential arterial hypertension, hypertension of the fifties, of menopause, of diabetics, of obesity and of plethoria as well as for the treatment of arterial hypertension due to old age, of artherosclerosis and for the treatment of hypertension of renal origin.

Among the preferred compounds are those wherein the active compounds of formula I have R as hydrogen as well as those wherein $R_1$ is hydrogen, chlorine or bromine, $R_2$ is alkyl of 1 to 4 carbon atoms and $R_3$ is —CH$_2$OH, —CH$_2$SCH$_3$, —CH$_2$CN, —COOH, —COOAlk or

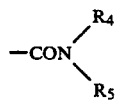

wherein Alk, $R_4$ and $R_5$ are alkyl of 1 to 4 carbon atoms and their acid addition salts.

Particularly preferred compounds are those containing as the active ingredient a compound selected from the group consisting of [6a RS (6aα,9β,10aβ)] 4,6,6a,8,9,10a-hexahydro-7-methyl-7H-indolo(3,4-g,h)1,4-benzoxazine-9-methanol, [6a RS (6aα,9β,10aβ)] N,N-diethyl-4,6,6a,8,9,10a-hexahydro-7-methyl-7H-indolo-(3,4-g,h)1,4-benzoxazine-9-carboxamide and [6a RS(6aα,9β,10aβ)]4,6,6a,8,9,10a-hexahydro-7-methyl-9-methylthiomethyl-7H-indolo (3,4-g,h)1,4-benzoxazine and their non-toxic, pharmaceutically acceptable acid addition salts. Some of the compounds also have vasodilatatory and antianoxia properties.

The novel method of the invention of inducing hypotensive and dopaminergic agonist activity in warm-blooded animals, including humans, comprises administering to animals an amount of at least one compound of formula I and their non-toxic, pharmaceutically acceptable acid addition salts sufficient to cause hypotensive and dopaminergic agonist activity. The compounds may be administered orally, rectally or parenterally and the usual daily dose will vary depending on the condition being treated, the specific compound and the method of administration. The usual daily dose is 0.07 to 2.8 mg/kg of compound of Example 2 for the treatment of Parkinson disease.

The compounds of formulae III and X are novel intermediates and are also an object of the invention.

In the following examples there are described several preferred embodiments to illustrate the invention. However, it should be understood that the invention is not intended to be limited to the specific embodiments.

EXAMPLE 1.

Methyl [6a RS (6aα,9β, 10aβ)] 4,6,6a,8,9,10a-hexahydro-7-methyl-7H-indolo-[3,4-g,h](1,4)-benzoxazine-9-carboxylate hydrochloride STEP A: 4RS trans 1,2,2a,3,4,5-hexahydro-4-methylamino-1-benzyl-benz(c,d)indo-5-ol 26 g of 4RS trans 4-amino-1-benzoyl-1,2,2a,3,4,5-hexahydro-benz(c,d)indol-5-ol were slowly added under an inert atmosphere with stirring to a mixture of 26 g of lithium aluminum hydride, 13 g of aluminum chloride and 800 ml of dioxane and the mixture was refluxed for 2 hours and cooled in an ice bath while adding dropwise 300 ml of 10% hydrated tetrahydrofuran and 300 ml of 2N sodium hydroxide solution. The mixture was vacuum filtered and the filter was washed with methylene chloride. The filtrate was added to 1.5 liters of methylene chloride and the organic phase was washed with water, dried and evaporated to dryness to obtain 20 g of 4RS trans 4-amino-1,2,2a,3,4,5-hexahydro-1-benzyl-benz(c,d)indol-5-ol melting at 166° C. after crystallization from methylene chloride.

10 g of the said product were dissolved in 100 ml of chloroform and 10 ml of sodium hydroxide and after cooling the mixture to 0° to 5° C., 25 ml of water were added thereto. Then, 4 ml of methyl chloroformate were added thereto dropwise and the mixture was stirred at room temperature for 30 minutes and was extracted with ethyl acetate containing 10% methanol. The organic phase was washed with aqueous saturated sodium chloride solution, dried and evaporated to dryness to obtain 11.8 g of product melting at 200° C. which was used as is.

A solution of 11.7 g of said product in 250 ml of tetrahydrofuran was added over 10 minutes at 0° to 5° C. to a suspension of 11.7 g of lithium aluminum hydride in 250 ml of tetrahydrofuran and the mixture was refluxed for 2 hours. 250 ml of 20% aqueous tetrahydrofuran were added thereto and the mixture was extracted with methylene chloride. The organic phase was washed with water, dried and evaporated to dryness to obtain 10 g of raw product. The said product was dissolved in 100 ml of methylene chloride and the mixture was stirred with activated carbon for 20 minutes. The methylene chloride phase was rinsed and concentrated to a volume of 100 ml. 100 ml of isopropyl ether were added thereto and the mixture stood at room temperature for 30 minutes and for 30 minutes in an ice bath to obtain 5.5 g of 4RS trans 1,2,2a,3,4,5-hexahydro-4-methylamino-1-benzyl-benz(c,d)indol-5-ol melting at 148° C.

STEP B: Ethyl 4RS trans 2-hydroxy-3-[(5-hydroxy-benzyl)-1,2,2a,3,4,5-hexahydro-benz(c,d)indol-4-yl)-methylamino]-propanoate A mixture of 24.2 g of the product of Step A, 1.2 liters of ethanol and 19.2 g of ethyl glycidate was refluxed under an inert atmosphere for 4 hours and was then evaporated to dryness under reduced pressure. The oil was chromatographed over silica gel and was eluted with a 7-3 benzene-ethyl acetate mixture to obtain 28.2 g of ethyl 4RS trans 2-hydroxy-3-[(5-hydroxy-benzyl)-1,2,2a,3,4,5-hexahydro-benz(c,d)indol-4-yl)-methylamino]-propanoate.

STEP C: Ethyl [6aRS (6aα,9β,10aβ)] and [6aRS (6aα,9β,10aβ)] 7-methyl-4,5,5a,6,6a,8,9,10a-octahydro-4-benzyl-7H-indolo-(3,4-g,h)(1,4)-benzoxazine-9-carboxylate 31.8 ml of hexamethylphosphoramine were added dropwise under an inert atmosphere at −40° to −45° C. to a solution of 22.6 g of the product of Step B, 17.25 g of N-chloro-diisopropylamine, and 200 ml of methylene chloride and the mixture was stirred for 15 minutes and then allowed to stand for one hour at room temperature. The mixture was poured into 250 ml of water and the organic phase was extracted with aqueous 2N hydrochloric acid. The aqueous phase was made alkaline with sodium hydroxide solution and was extracted with methylene chloride. The organic extract was washed with water, dried and evaporated to dryness under reduced pressure. The residue was added to a few ml of isopropyl ether and was vacuum filtered. The product was dried to obtain 9.6 g of the 9α-isomer of the desired compound melting at ≡ 156° C. The mother liquors were chromatographed over silica gel and eluted with a 7-3 benzene-ethyl acetate mixture to obtain another 2.2 g of the 9α-isomer melting at ≈157° C. and 3.4 g of the 9β-isomer melting at ≈110° C.

STEP D: Methyl [6a RS (6aα,9β,10aβ)] 7-methyl-4,5,5a,6,6a,8,9,10a-octahydro-4-benzyl-7H-indolo[3,4-g,h]benzoxazine-9β-carboxylate A mixture of 14.5 g of the isomer mixture of Step C, 1 liter of ethanol, 3.6 g of sodium in 200 ml of ethanol was refluxed for one hour under an inert atmosphere and was evaporated to dryness under reduced pressure. The residue was added to 50 ml of water and concentrated hydrochloric acid was added thereto to adjust the pH to 6.5. The mixture was evaporated to dryness under reduced pressure at 50° C. and the residue was taken up in 1.2 liters of methylene chloride and 50 ml of methanol. 300 ml of a solution of 12 g/l of diazomethane in methylene chloride was added dropwise at 5° to 10° C. to the mixture which was then stirred at 4° C. for 16 hours. Excess diazomethane was destroyed by addition of a few drops of acetic acid and the mixture was washed with 2N sodium hydroxide solution, with water, dried and evaporated to dryness under reduced pressure. The residue was added to a few ml of ether and the mixture was vacuum filtered. The product was dried to obtain 11.8 g of methyl [6a RS (6aα,9β,10aβ)] 7-methyl-4,5,5a,6,6a,8,9,10a-octahydro-4-benzyl-7H-indolo[3,4-g,h]benzoxazine-9β-carboxylate melting at ≈127° C. and at 130° C. after crystallization from isopropyl ether.

Analysis: $C_{24}H_{28}N_2O_3$; molecular weight=378.46; Calculated: %C 72.99, %H 6.92, %N 7.40; Found: %C 72.7, %H 7.0, %N 7.3.

STEP E: Methyl [6a RS (6aα,9β,10aβ)] 7-methyl-4,5,5a,6,6a,8,9,10a-octahydro-7H-indolo[3,4-g,h](1,4)-benzoxazine-9-carboxylate A mixture of 12.75 g of methyl [6a RS (6aα,9β,10aβ)] 4,5,5a,6,6a,8,9,10a-octahydro-7-methyl-4-benzyl-7H-indolo[3,4-g,h](1,4)-benzoaxazine-9-carboxylate, 600 ml of acetic acid and 3.2 g of 10% palladized activated carbon was hydrogenated for 4 hours and the mixture was filtered. The filter was rinsed with acetic acid and the filtrate was evaporated to dryness at 30°-35° C. under reduced pressure. The residue was added to 200 ml of water and the mixture was adjusted to a pH of 9 by addition of ammonium hydroxide. The mixture was extracted with methylene chloride and the organic phase was washed with water, dried and evaported to dryness under reduced pressure. The residue was added to a few ml of ether and the mixture was vacuum filtered. The product was dried at 50° C. under reduced pressure to obtain 8.28 g of methyl [6a RS (6aα,9β,10aβ)] 7-methyl-4,5,5a,6,6a,8,9,10a-octahydro-7H-indolo [3,4-g,h](1,4)benzoazine-9-carboxylate melting at 178° C. Chromatography of the mother liquors over silica gel and elution with a 95-5 chloroform-methanol mixture yielded another 0.475 g of the product melting at ≈178° C.

STEP F: Methyl [6a RS (6aα,9β,10aβ)] 4,6,6a,8,9,10a-hexahydro-7-methyl-7H-indolo[3,4-g,h](1,4)benzoxazine-9-carboxylate A mixture of 33.5 g of manganese dioxide and a solution of 8.4 g of the product of Step E in 840 ml of methylene chloride was stirred under an inert atmosphere for 16 hours and was filtered. The filtrate was washed and evaporated to dryness under reduced pressure. The residue was added to a few ml of ether and the mixture was vacuum filtered. The product was dried to obtain 2 crops of 3.9 and 0.91 g of methyl [6a RS (6aα,9β,10aβ)] 4,6,6a,8,9,10a-hexahydro-7-methyl-7H-indolo[3,4-g,h](1,4)benzoxazine-9-carboxylate melting at 174° C. and an additional 1.1 g of product melting at 174° C. by chromatography of the mother liquors.

2 g of the said base were dissolved in 50 ml of hot methanol and 5 ml of 2N methanolic hydrochloric acid were added thereto. The mixture was filtered and the product was washed with methanol, dried at 50° C. under reduced pressure and crystallized from methanol to obtain 1.78 g of the hydrochloride of the said base melting at 248° C. (with decomposition).

Analysis: $C_{16}H_{18}N_2O_3HCl$; molecular weight=322.78; Calculated: %C 59.53, %H 5.93, %N 8.68, %Cl 10.98; Found: %C 59.3, %H 6.1, %N 8.5, %Cl 10.8.

EXAMPLE 2

[6a RS
(6aα,9β,10aβ)]4,6,6a,8,9,10a-hexahydro-7-methyl-7H-indolo[3,4-g,h](1,4)benzoxazine-9-methanol and its hydro-chloride A mixture of 2.2 g of the free base of Example 1, 30 ml of dioxane, 15 ml of methanol and 2.2 g of 95% sodium borohydride was refluxed with stirring under an inert atmosphere for one hour and after cooling the mixture, 150 ml of water were added thereto. The mixture was extracted with methylene chloride and the organic phase was washed with water, dried and filtered. The filtrate was evaporated to dryness under reduced pressure and the residue was added to a few ml of ether. The mixture was vacuum filtered and the product was dried at 50° C. under reduced pressure to obtain 1.82 g and then 0.08 g of [6a RS (6aα,9β,10aβ)] 4,6,6a,8,9,10a-hexahydro-7-methyl-7H-indolo[3,4-g,h](1,4-benzoxazine-9-methanol melting at 208° C.

2 g of the free base were dissolved in 80 ml of methanol and 5 ml of methanolic 2N hydrochloric acid were added thereto. The mixture stood for 16 hours and was vacuum filtered. The product was rinsed with ether and dried at 50° C. under reduced pressure to obtain 1.97 g of the hydrochloride of the said base melting at 320° C.

Analysis: $C_{15}H_{18}N_2O_2.HCl$; molecular weight=294.77; Calculated: %C 61.11, %H 6.50, %N 9.50, %Cl 12.03; Found: %C 61.0, %H 6.5, %N 9.3, %Cl 12.2.

EXAMPLE 3

[6a RS (6aα,9β,10aβ)]
4,6,6a,8,9,10a-hexahydro-7-methyl-7H-indolo[3,4-g,h](1,4)-benzoxazine-9-carboxylic acid A mixture of 1.61 g of the free base of Example 1, 170 ml of methanol and 520 mg of sodium was refluxed under an inert atmosphere for 3 hours and was then evaporated to dryness under reduced pressure. The residue was added to a few ml of water and acetic acid was added to adjust the pH to about 6.4. The mixture was vacuum filtered and the product was washed with water, then acetone and dried to obtain 1.5 g of [6a RS (6aα,9β,10aβ)]4,6,6a,8,9,10a-hexahydro-7-methyl-7H-indolo [3,4-g,h](1,4)-benzoxazine-9-carboxylic acid

EXAMPLE 4

[6a RS
(6aα,9β,10aβ)]N,N-diethyl-4,6,6a,8,9,10a-hexahydro-7-methyl-7H-indolo
[3,4-g,h](1,4)benzoxazine-9-carboxamide 1.3 ml of tributylamine and 0.63 ml of isobutyl chloroformate were added to a solution of 1.22 g of the acid of Example 3 in 30 ml of dimethylformamide and the mixture was stirred under an inert atmosphere at 20° C. for one hour and then was then poured into 30 ml of dioxane containing 2.7 ml of diethylamine. The mixture was stirred under an inert atmosphere for one hour and was added to 100 ml of water. The mixture was extracted with methylene chloride and the organic phase was washed with water, dried and evaporated to dryness under reduced pressure. The residue was chromatographed over silica gel and eluted with a 95-5 chloroform-methanol mixture to obtain 1.03 g of [6a RS (6aα,9β,10aβ)] N,N-diethyl-4,6,6a,8,9,10a-hexahydro-7-methyl-7H-indolo[3,4-g,h](1,4) benzoxazine-9-carboxamide melting at ≃210° C. and then 150 mg melting at ≃210° C.

1.18 g of the said base was dissolved in 50 ml of methanol and the solution was cooled to 10° to 15° C. after which 5 ml of methanolic 2N hydrochloric acid were added. Crystallization was effected for 16 hours and the mixture was vacuum filtered. The product was washed and dried under reduced pressure to obtain 1.07 g of the hydrochloride of the base melting at >250° C.

Analysis: $C_{19}H_{25}N_3O_2.HCl$; molecular weight=363.87; Calculated: %C 62.70, %H 7.20, %N 11.55, %Cl 9.74; Found: %C 62.4, %H 7.2, %N 11.5, %Cl 10.0.

EXAMPLE 5

[6a RS
(6aα,9β,10aβ)]N,N-diethyl-4,6,6a,8,9,10a-hexahydro-5-bromo-7-methyl-7H-indolo(3,4-g,h)1,4-benzoxazine-9-carboxamide A solution of 14.6 g of pyrrolidone hydrotribromide in 1.8 liters of dioxane was added over 20 minutes at 25° C. to a solution of 6.43 g of the product of Example 4 in 1.6 liters of dioxane and the mixture was stirred for 30 minutes and then was evaporated to dryness at 35° C. maximum. The residue was dissolved in methylene chloride and the solution was washed with aqueous saturated sodium bicarbonate solution, then with water, dried and evaporated to dryness under reduced pressure. The residue was chromatographed over silica gel and eluted with a 4-4-2 cyclohexane-chloroform-triethylamine mixture. The product was crystallized from ether to obtain 5.7 g of [6a RS (6aα,9β,10aβ)]N,N-diethyl-4,6,6a,8,9,10a-hexahydro-5-bromo-7-methyl-7H-indolo(3,4-g,h)1,4-benzoxazine-9-carboxamide melting at >250° C.

The said product was suspended in 100 ml of methanol and 20 ml of a methanolic 1.4N hydrochloric acid solution was added thereto with stirring and cooling. The mixture was stirred at 20° C. for two hours and was vacuum filtered. The crystals were washed with methanol, then with ether and dried to obtain 4.38 g of the hydrochloride of the base melting at >250° C.

Analysis: $C_{19}H_{24}BrN_3O_2.HCl$; Calculated: %C 51.54, %H 5.69, %N 9.49, %Cl 8.01, %Br 18.05; Found: %C 51.8, %H 5.7, %N 9.5, %Cl 8.5, %Br 17.7.

EXAMPLE 6

[6a RS
(6aα,9β,10aβ)]N,N-dimethyl-4,6,6a,8,9,10a-hexahydro-7-methyl-7H-indolo(3,4-g,h)1,4-benzoxazine-9-carboxamide and its hydrochloride Using the procedure of Example 4, 40% aqueous dimethylamine was reacted to obtain after crystallization from isopropyl ether a 75% yield of [6a RS (6aα,9β,10aβ)]N,N-dimethyl-4,6,6a,8,9,10a-hexahydro-7-methyl-7H-indolo(3,4-g,h)1,4-benzoxazine-9-carboxamide melting at 228° C. Its hydrochloride melted at 296° C. (decomposition).

EXAMPLE 7

[6a RS
(6aα,9β,10aβ)]N-piperidinyl-4,6,6a,8,9,10a-hexahydro-7-methyl-7H-indolo(3,4-g,h)1,4-benzoxazine-9-carboxamide and its hydrochloride Using the procedure of Example 4, piperidine was reacted to obtain after crystallization from methanol a 70% yield of [6a RS (6aα,9β,10aβ)]N-piperidinyl-4,6,6a,8,9,10a-hexahydro-7-methyl-7H-indolo(3,4-g,h)1,4-benzoxazine-9-carboxamide melting at 215° C. Its hydrochloride melted at 296° C.

EXAMPLE 8

[6a RS (6aα,9β,10aβ)]4,6,6a,8,9,10a-hexahydro-7-methyl-9-methylthiomethyl-7H-indolo(3,4-g,h)1,4-benzoxazine and its hydrochloride

STEP A: [6a RS (6aα,9β,10aβ)]4,6,6a,8,9,10a-hexahydro-7-methyl-7H-indolo(3,4-g,h)1,4-benzoxazine-9-p-toluenesulfonatemethanol A solution of 9.5 g of tosyl chloride in 125 ml of pyridine was added to a mixture of 6.6 g of the product of Example 2 and 66 ml of pyridine and the mixture was stirred at 20° C. for 17 hours and was then poured into methylene chloride. The mixture was washed with aqueous saturated sodium bicarbonate solution, dried and evaporated to dryness. The residue was chromatographed over silica gel and was eluted with a 95-5 methylene chloride-methanol mixture to obtain 7.7 g of [6a RS (6aα,9β,10aβ)]4,6,6a,8,9,10a-hexahydro-7-methyl-7H-indolo(3,4-g,h)1,4-benzoxazine-9-p-toluenesulfonate-methanol which after crystallization from an isopropyl ether-methylene chloride mixture melted at 180° C.

STEP B: [6a RS (6aα,9β,10aβ)]4,6,6a,8,9,10a-hexahydro-7-methyl-9-methylthiomethyl-7H-indolo(3,4-g,h)1,4-benzoxazine and its hydrochloride 50 ml of condensed methylmercaptan were added to 150 ml of dimethylacetamide at 0° C. and then 12.6 g of sodium hydride as a 50% mineral oil mixture were added thereto. A solution of 6.6 g of the product of Step A in 40 ml of dimethylacetamide were added over 15 minutes at 20° C. to the mixture and the mixture was stirred for 2 hours and was poured into iced water. The mixture was extracted with methylene chloride and the organic phase was washed with water, dried and evaporated to dryness. The residue was chromatographed over silica gel and eluted with a 95-5 methylene chloride-methanol mixture to obtain a 4.2 g of [6a RS (6aα,9β,10aβ)] 4,6,6a,8,9,10a-hexahydro-7-methyl-9-methylthiomethyl-7H-indolo (3,4,-g,h)1,4-benzoxazine which melted at 150° C. after crystallization from methylene chloride.

3.96 g of the said base were dissolved in 150 ml of methylene chloride and 7 ml of hydrochloric acid in ether were added thereto. Crystallization was effected at 20° C. and the mixture was vacuum filtered. The crystals were washed with methylene chloride and dried to obtain 4.1 g of the hydrochloride of the base which melted at 250° C. (decomposition) after crystallization from methanol.

Analysis: $C_{16}H_{10}N_2OS.HCl$; Calculated: %C 59.15, %H 6.52, %N 8.62, %S 9.87, %Cl 10.91; Found: %C 58.7, %H 6.6, %N 8.7, %S 9.8, %Cl 10.9.

EXAMPLE 9

[6a RS (6aα,9β,10aβ)]4,6,6a,8,9,10a-hexahydro-7-methyl-9-cyanomethyl-7H-indolo(3,4-g,h)1,4-benzoxazine and its hydrochloride 13.9 g of sodium cyanide, 40 ml of dimethylformamide and 20 ml of water were added to a solution of 6.2 g of the product of Step A of Example 8 in 30 ml of dimethylformamide and the mixture was stirred at 65° C. for 17 hours. The mixture was cooled and poured into water. The mixture was extracted with methylene chloride containing 10% of methanol and the organic phase was washed with water, dried and evaporated to dryness. The residue was crystallized from ether and then from methylene chloride to obtain 3.5 g of [6a RS (6aα,9β,10aβ)]4,6,6a,8,9,10a-hexahydro-7-methyl-9-cyanomethyl-7H-indolo(3,4-g,h)1,4-benzoxazine melting at 250° C.

A solution of 3.5 g of the said base in 700 ml of methanol was concentrated and 10 ml of a solution of hydrogen chloride in ether were added thereto. Crystallization was effected at 20° C. and the mixture was filtered. The crystals were dried to obtain 3.6 g of the hydrochloride of the said base melting at 225° C.

Analysis: $C_{16}H_{17}N_3O.HCl$; Calculated: %C 63.25, %H 5.97, %N 13.83, %Cl 11.67; Found: %C 63.2, %H 6.0, %N 13.6, %Cl 11.8.

EXAMPLE 10

Tablets were prepared containing 5 mg of [6a RS (6aα,9β,10aβ)]4,6,6a,8,9,10a-hexahydro-7-methyl-7H-indolo(3,4-g,h)1,4-benoxazine-9-methanol hydrochloride or 10 mg of [6a RS (6aα,9β,10aβ)]N,N-diethyl-4,6,6a,8,9,10a-hexahydro-7-methyl-7H-indolo(3,4-g,h)1,4-benzoxazine-9-carboxamide hydrochloride or 5 mg of [6a RS (6aα,9β,10aβ)]4,6,6a,8,9,10a-hexahydro-7-methyl-9-methylthiomethyl-7H-indolo(3,4-g,h)1,4-benzoxazinehydrochloride and sufficient excipient of lactose, starch, talc and magnesium stearate for a final weight of 100 mg.

PHARMACOLOGICAL DATA

A. Rotation behavior after unilateral injury of nigrostriatal bundle

The unilateral lesion was effected with male rats weighing about 220 g by unilateral injection into nigrostriatal dopamingeric bundle of 8 μg of 6-hydroxydopamine in a solution of 2 μg per μl by the method of Ungerstedt [Acta. Physiol. Scand., Vol. 82 (1971), supp. 367, p.69–93]. In the animals, the direct dopaminergic agonists such as apomorphine administered generally induces a rotating behavior in the contralateral direction to the injured side. The test compounds were administered more than 5 weeks after the lesion and the rats were placed in an automatic rotometer which determined the number of rotations effected by each animal in 2 directions. The compounds of Examples 2,4,8 and 9 administered intraperitoneally provoked contralateral rotations at a dose of 0.1, 0.1, 0.5 and 0.2 mg/kg respectively.

B. Hypotensive Activity

The hypotensive activity was studied on male rats of the Wistar strain weighing about 300 g and anesthesized with nembutal (50 mg/kg-intravenously). The test compound was administered intravenously through the jugular vein and carotidine arterial pressure was measured before and after the test product administration. The arterial pressure difference were calculated as in Table I and the results are reported in Table I.

TABLE I

| Product of Example | Dose in mg/kg | % arterial pressure variation after minutes | | | |
|---|---|---|---|---|---|
|  |  | 1 | 5 | 10 | 30 |
| 1 | 1 | −2 | −2 | −4 | −10 |

TABLE I-continued

| Product of Example | Dose in mg/kg | % arterial pressure variation after minutes | | | |
|---|---|---|---|---|---|
| | | 1 | 5 | 10 | 30 |
| 2 | 1 | −24 | −30 | −32 | −25 |
| | 0.1 | −13 | −12 | −14 | −9 |
| 4 | 1 | −13 | −6 | −6 | −20 |
| 8 | 1 | −26 | −35 | −39 | −40 |
| | 0.1 | −10 | −11 | −12 | −16 |
| 9 | 0.1 | −24 | −24 | −23 | −22 |
| | 0.01 | −10 | −9 | −10 | −11 |

C. Cerebral blood flow rate

The cerebral blood flow rate was measured by the technique of hydrogen purge by the polarographic method of Auckland [Circulation Research, Vol. 14 (1964), p. 164–187]. The electrodes used to determine the tissue concentration of hydrogen were obtained by introducing a platinum wire with a 125 μm diameter into a drawn glass tube followed by a platinization at the point by electrolysis in a 5% aqueous chloroplatinic acid solution.

The tests were effected on male Wistar rats weighing between 300 and 430 g in a free situation in a bottle measuring 20×20 cm and having a height of 24 cm. The hydrogen electrode was implanted in the right frontal cortex to a depth of 0.5 mm with an anteriority of 2.0 mm and a laterality of 2.0 mm with respect to the bregma. The implantation was effected with a general anesthesia (sodium pentobarbital—50 mg/kg i.p.) a few days before the start of the test. The reference electrode was introduced at dura mater in the symetrical region of the contralateral cortex. Before the intraperitoneal administration of the test compound, the blood flow was measured 4 times every 15 minutes. Analysis of the variance of the values produced by the product assured that the values were homogeneous. The average of the 4 values was obtained to obtain the blood flow value. The blood flow was also measured 5,15,30,45 and 60 minutes after the administration of the product intraperitoneally and the values of Table II are expressed in percentage of increase of the cerebral blood flow.

TABLE II

| Product of Example | Dose in mg/kg | % variation of blood flow in minutes per administration | | | | |
|---|---|---|---|---|---|---|
| | | 5 | 15 | 30 | 45 | 60 |
| 8 | 10 | +53 | +70 | +75 | +22 | +35 |
| 9 | 10 | +192 | +130 | +129 | +128 | +120 |

D. Acute toxicity

The acute toxicity was determined on groups of mice who intraperitoneally received the test compounds to determine the $DL_0$ dose or the maximum dose at which no mice were killed after 8 days. The $DL_0$ results for the products of Examples 1,2,4,8,9 were 100, 80, >400, ≧400 and 200 mg/kg respectively.

Various modifications of the products and processes of the invention may be made without departing from the spirit or scope thereof and it should be understood that the invention is intended to be limited only as defined in the appended claims.

What we claim is:

1. A compound selected from the group consisting of

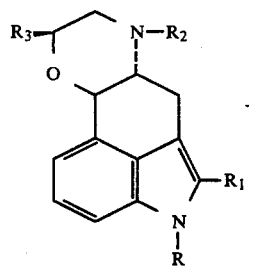

wherein R is selected from the group consisting of hydrogen and alkyl of 1 to 4 carbon atoms, $R_1$ is selected from the group consisting of hydrogen, chlorine and bromine, $R_2$ is selected from the group consisting of hydrogen, alkyl of 1 to 4 carbon atoms, aralkyl of 7 to 12 carbon atoms and cycloalkylalkyl of 4 to 7 carbon atoms, $R_3$ is selected from the group consisting of —CH$_2$OH, alkylthiomethyl with 1 to 4 alkyl carbon atoms, —CH$_2$CN, —COOH, —COOAlk and

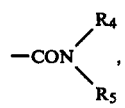

Alk is alkyl of 1 to 5 carbon atoms, $R_4$ is selected from the group consisting of hydrogen and alkyl of 1 to 4 carbon atoms, $R_5$ is alkyl of 1 to 4 carbon atoms or $R_4$ and $R_5$ together with the nitrogen form a saturated heterocycle optionally containing another heteroatom and their non-toxic, pharmaceutically acceptable acid addition salts.

2. A compound of claim 1 wherein R is hydrogen.

3. A compound of claim 2 wherein $R_1$ is hydrogen, chlorine or bromine, $R_2$ is alkyl of 1 to 4 carbon atoms and $R_3$ is —CH$_2$OH, —CH$_2$SCH$_3$, —CH$_2$CN, —COOH,

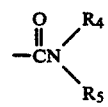

or —COOAlk, Alk is alkyl of 1 to 4 carbon atoms and $R_4$ and $R_5$ are alkyl of 1 to 4 carbon atoms.

4. A compound of claim 1 selected from the group consisting of [6a RS (6aα,9β,10aβ)]4,6,6a,8,9,10a-hexahydro-7-methyl-7H-indolo(3,4-g,h)1,4-benzoxazine-9-methanol, [6a RS (6aα,9β,10aβ)]N,N-diethyl-4,6,6a,8,9,10a-hexahydro-7-methyl-7H-indolo-(3,4-g,h)1,4-benzoxazine-9-carboxamide and [6a RS (6aα,9β,10aβ)]4,6,6a,8,9,10a-hexahydro-7-methyl-9-methylthiomethyl-7H-indolo(3,4-g,h)1,4-benzoxazine and their non-toxic, pharmaceutically acceptable acid addition salts.

5. A compound selected from the group consisting of

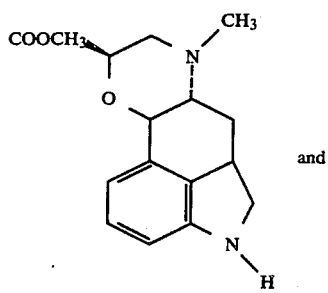

and

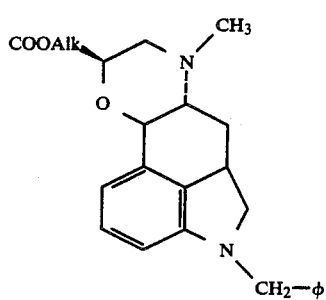

wherein Alk is alkyl of 1 to 4 carbon atoms.

6. An antihypertensive and dopaminergic agonist compositions comprising an antihypertensively and dopaminergic agonistically effective amount of at least one compound of claim 1 and an inert carrier.

7. A composition of claim 6 wherein R is hydrogen.

8. A composition of claim 6 wherein $R_1$ is hydrogen, chlorine or bromine, $R_2$ is alkyl of 1 to 4 carbon atoms and $R_3$ is —CH$_2$OH, —CH$_2$SCH$_3$, —CH$_2$CN, —COOH,

or —COOAlk, Alk is alkyl of 1 to 5 carbon atoms and $R_4$ and $R_5$ are alkyl of 1 to 4 carbon atoms.

9. A composition of claim 6 wherein the active compounds is selected from the group consisting of [6a RS(6aα,9β,10aβ)]4,6,6a,8,9,10a-hexahydro-7-methyl-7H-indolo(3,4-g,h) 1,4-benzoxazine-9-methanol, [6a RS (6aα,9β,10aβ)]N,N-diethyl-4,6,6a,8,9,10a-hexahydro-7-methyl-7H-indolo-(3,4-g,h)1,4-benzoxazine-9-carboxamide and [6a RS (6aα,9β,10aβ)]4,6,6a,8,9,10a-hexahydro-7-methyl-9-methylthiomethyl-7H-indolo(3,4-g,h) 1,4-benzoxazine and their non-toxic, pharmaceutically acceptable acid addition salts.

10. A method of inducing antihypertensive and dopaminergic agonist activity in warm-blooded animals comprising administering to warm-blooded animals an amount of at least one compound of claim 1 sufficient to cause antihypertensive and dopaminergic activity.

11. A method of claim 10 wherein R is hydrogen.

12. A method of claim 10 wherein $R_1$ is hydrogen, chlorine or bromine, $R_2$ is alkyl of 1 to 4 carbonatoms and $R_3$ is —CH$_2$OH, —CH$_2$SCH$_3$, —CH$_2$CN, —COOH,

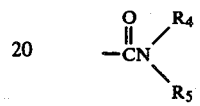

or —COOAlk, Alk is alkyl of 1 to 5 carbon atoms and $R_4$ and $R_5$ are alkyl of 1 to 4 carbon atoms.

13. A method of claim 10 wherein the active compounds is selected from the group consisting of [6a RS(6aα,9β,10aβ)]4,6,6a,8,9,10a-hexahydro-7-methyl-7H-indolo(3,4-g,h) 1,4-benzoxazine-9-methanol, [6a RS (6aα,9β,10aβ)]N,N-diethyl-4,6,6a,8,9,10a-hexahydro-7-methyl-7H-indolo-(3,4-g,h)1,4-benzoxazine-9-carboxamide and [6a RS (6aα,9β,10aβ)]4,6,6a,8,9,10a-hexahydro-7-methyl-9-methylthiomethyl-7H-indolo(3,4-g,h) 1,4-benzoxazine and their non-toxic, pharmaceutically acceptable acid addition salts.

14. A method of treating hypersecretion of prolactin in warm-blooded animals comprising administering to warm-blooded animals an amount of at least one compound of claim 1 sufficient to prevent hypersecretion of prolactin.

15. The method of claim 14 wherein R is hydrogen.

16. A method of treating cerebral hypoxia in warm-blooded animals comprising administering to warm-blooded animals an amount of at least one compound of claim 1 sufficient to treat cerebral hypoxia.

17. The method of claim 16 wherein R is hydrogen.

* * * * *